United States Patent [19]

Sweet

[11] Patent Number: 5,700,692
[45] Date of Patent: Dec. 23, 1997

[54] FLOW SORTER WITH VIDEO-REGULATED DROPLET SPACING

[75] Inventor: Richard G. Sweet, Palo Alto, Calif.

[73] Assignee: Becton Dickinson and Company, Franklin Lakes, N.J.

[21] Appl. No.: 312,592

[22] Filed: Sep. 27, 1994

[51] Int. Cl.$^6$ .............................. B07C 5/02; G01N 15/00
[52] U.S. Cl. .................. 436/50; 436/43; 436/55; 436/164; 422/68.1; 422/73; 422/105; 209/577; 209/588; 209/638; 209/939
[58] Field of Search ................... 436/63, 50, 43, 436/52, 164, 55, 807, 10; 422/68.1, 73, 81, 105; 209/3.1, 3.2, 552, 576, 577, 587, 638, 588, 939

[56] References Cited

U.S. PATENT DOCUMENTS

| | | | |
|---|---|---|---|
| 3,826,364 | 7/1974 | Bonner et al. | 209/3 |
| 3,907,429 | 9/1975 | Kuhn et al. | 356/28 |
| 3,963,606 | 6/1976 | Hogg | 209/3.1 |
| 4,007,463 | 2/1977 | Fujimoto et al. | 346/75 |
| 4,012,745 | 3/1977 | Brown et al. | 346/1 |
| 4,047,183 | 9/1977 | Taub | 346/1 |
| 4,318,483 | 3/1982 | Lombardo et al. | 209/3.1 |
| 4,325,483 | 4/1982 | Lombardo et al. | 209/3.1 |
| 4,361,400 | 11/1982 | Gray et al. | 356/23 |
| 4,981,580 | 1/1991 | Auer | 209/3.1 |
| 5,030,002 | 7/1991 | North, Jr. | 356/73 |
| 5,101,978 | 4/1992 | Marcus | 209/3.1 |
| 5,180,065 | 1/1993 | Touge et al. | 209/577 |
| 5,483,469 | 1/1996 | Van Den Engh et al. | 364/555 |

OTHER PUBLICATIONS

"FACS Vantage", Becton–Dickinson and Company, 1992.
Herzenberg, Lenard A., Richard G. Sweet, Lenore A. Herzenberg, "Fluorescence–activated Cell Sorting" *Scientific American*, vol. 234, No. 3, pp. 108–117.
Horan, Paul K., Leon L. Wheeler, Jr., "Quantitative Single Cell Analysis and Sorting" *Science*, vol. 198, Oct. 14, 1977, pp. 149–157.

*Primary Examiner*—Long V. Le
*Attorney, Agent, or Firm*—Allen W. Wark

[57] ABSTRACT

A droplet-deflection flow sorter images a series of droplets, analyzes the image to determine droplet spacing, and alters flow velocity to achieve a desired spacing. Cells in a suspension are forced by gas pressure into a narrow conduit to serialize them and then out a nozzle that includes a "window" that allows cells of interest to be characterized. Droplets breaking off from the exiting jet are imaged by a video system including a strobed light source and a video camera. Droplet spacing is determined by locating the centers of gravity of the droplets. The centers of gravity are located by processing the droplet images to produce line segments corresponding to volumetric droplet slices, with the relative volumes of the slices being proportional to the squares of the line segment lengths. This approach determines droplet center positions and thus spacing more accurately than non-imaging methods, especially with aspherical droplets and droplets with satellites. The actual droplet spacing is compared to desired spacing, and the pressure regulator is adjusted accordingly. Synchronously, voltage is applied to droplets of interest. The droplets pass between a pair of deflection plates with a potential difference between them, so that charged droplets containing cells of interest are deflected and gathered while uncharged droplets not containing such cells are not deflected.

4 Claims, 3 Drawing Sheets

FLOW SORTER WITH VIDEO-REGULATED DROPLET SPACING

BACKGROUND OF THE INVENTION

The present invention relates to biomedical instrumentation and methods and, more particularly, to flow sorting of particles. A major objective of the present invention is to provide for a high-throughput, automated flow cytometry system.

Sorting biological cells by their characteristics provides relatively pure samples for study for both biomedical research and clinical medicine. Bulk cell sorting techniques rely on: selective destruction, selective stimulation, adherence, filtration, countercurrent distribution, electrophoresis, sedimentation, and centrifugation. These bulk techniques are limited to separating cells with suitably distinct physical properties. Furthermore, as a group, bulk cell sorting techniques are characterized by relatively high throughput, but relatively low selectivity. When higher target purity is required, cells can be sorted one-by-one using flow sorting techniques.

Flow sorters begin with a cell suspension. This suspension is made to flow in a stream in which the cells are serialized. One or more detectors are used to characterize passing cells, and thus to identify cells of interest. These cells are physically removed from the flowing suspension downstream of the detections. Flow sorters are described in "Flow Sorters for Biological Cells" by Tore Lindmo, Donald C. Peters, and Richard G. Sweet, *Flow Cytometry and Sorting*, 2d ed. (New York: Wiley-Liss, Inc., 1990), pages 145–169.

Fluidic switching flow sorters remove cells by momentarily diverting the liquid stream when the cell of interest reached a diversion point. Several mechanisms have been devised to implement the switching. As a class, fluidic switching flow sorters are characterized by an inherently slow separation rate. Accordingly, they have been practically limited to isolating small numbers of cells for further analysis, and to enriching for infrequently occurring cells.

Higher flow sorting rates have been attained using deflected droplet sorters, which have been commercially available since 1975. Deflected droplet sorters employ techniques originally developed for ink jet printers. As with fluidic switching sorters, cells are characterized and identified in stream. The stream is then broken into a series of droplets. The droplet generator imposes periodic pressure variations on the fluid stream. This variation can be implemented by deforming an exit chamber under the influence of a piezo-electrically driven lever. The resulting periodic expansion and contraction of the chamber periodically perturbs the fluid pressure so droplets are generated at the perturbation rate.

Deflected-droplet sorters divert discrete droplets rather than segments of a continuous stream. Just prior to the separation of a droplet containing a cell of interest, a voltage is applied to the stream so that the drop assumes a predetermined charge. A series of such droplets is passed through a strong electric field; charged droplets are deflected by the field, while uncharged droplets retain their original trajectory. The deflected cells can then be collected separately from the undeflected cells.

The cell transit time between the detection section and the droplet breakoff point must be known precisely to ensure that the droplet containing a cell of interest is properly charged. This transit time can vary with cell path length differences, variations in droplet breakoff point, and variations in flow velocity.

Most deflected droplet systems use a coaxial flow arrangement to minimize path length differences and the effects of nozzle walls on cell velocity. In such systems, the cell suspension constitutes only a small fraction of the total fluid in the flow system. The cell suspension is injected along the axis of a converging and accelerating sheath of cell-free fluid at a point where the fluid velocity is low and the cross-sectional area is relatively high. Provided laminar flow and radial symmetry are maintained, cells do not contact the nozzle wall. Cells are confined to a fraction of the flow cross section, minimizing path-length variations between the detection section and the droplet separation.

The droplet breakoff point is determined by the amplitude of the droplet generator. The droplet breakoff point can be located by examining a strobe-illuminated video image of the fluid jet and the droplets. Typically, the phase of the droplet generator is adjusted relative to the strobe so that the first droplet in each video frame assumes a predetermined fixed position. The drive amplitude is then adjusted to achieve a predetermined spacing, selected to correspond to a desired breakoff point between the first droplet in the video frame and the liquid jet from which it was formed.

The flow velocity is typically established by a gas pressure applied to the suspension and sheathing fluid. Changes in flow velocity can be detected as changes in droplet spacing. Thus, droplet spacing can be used as a parameter in a feedback loop to regulate flow velocity.

For example, U.S. Pat. No. 3,907,429 to Kuhn et al. describes a system in which the droplets pass by a pair of apertures. The apertures are spaced along the droplet trajectory a distance less than the nominal droplet spacing. The passing droplets are illuminated by a strobe, the frequency of which is different from the droplet generation frequency. The time between when the first aperture is blocked by a droplet (as indicated by the light being broken during a strobe) and when the second aperture is blocked by a droplet gives the droplet velocity; droplet spacing can be determined from this velocity and the drive frequency. If the calculated spacing differs from the desired spacing, the pressure driving the liquid stream is varied accordingly.

Despite these attempts to minimize cell path differences using a sheathing flow, to control the breakoff point using video feedback, and to regulate flow velocity using optical feedback, uncertainties in transit time limit cell throughput as follows. To ensure that a cell of interest is in a deflected droplet, a greater-length stream segment must be diverted (for example, by deflecting more than one droplet per cell). The greater volume being diverted increases the probability that an unwanted cell will also be diverted. To decrease the chances of such a "coincidence", a more dilute suspension can be used. However, this means that fewer cells are sorted per unit time, i.e., throughput is reduced.

The direct effects of limited throughput include delayed research results and reduced utility for clinical purposes. Indirect effects include higher costs for equipment time and operation. What is needed is a system and method for flow cytometry which retains a high level of cell selectivity while providing for increased sorting throughput.

SUMMARY OF THE INVENTION

In accordance with the present invention, a droplet-deflection flow sorter includes a strobed video or other video system to obtain an image of a series of droplets. This image is analyzed to determine droplet spacing. The result is compared with the desired droplet spacing. Flow velocity is altered, as necessary, to reduce this difference. Acquisition of images, image analysis, and velocity adjustments can be ongoing to maintain flow velocity at a desired magnitude.

The droplet-deflection flow sorter includes means for serializing a cell (or other particle) suspension in a liquid stream, detection means for characterizing particles, electric field means for applying an electric field to the stream, a droplet generator, means for producing an electric field to deflect charged droplets, and collection means for collecting deflected droplets. The imaging system includes image acquisition hardware and a video processor that determines deviations of actual droplet spacing from a target value.

The method of the invention involves serializing the cells in the stream, characterizing the cells, conveying the cells to a breakoff point, charging the stream so that the droplet containing a cell of interest is appropriately charged at breakoff, deflecting the droplets as a function of charge, and collecting droplets according to their deflection. While the droplets are traversing their trajectories, a strobed image can be obtained. This image includes subimages of individual droplets.

The subimages can be analyzed to locate the droplet centers. Preferably, the centers are the centers of gravity (or mass). The center of gravity for each droplet image can located by assuming that the droplet image represents a droplet that has cylindrical symmetry about its trajectory. The spacing of the droplet centers can be used to calculate droplet spacing. This droplet spacing can be compared with a desired value. The flow pressure can be adjusted to establish and maintain the desired droplet spacing.

The present invention provides at least an order of magnitude improvement in the precision with which deviations from desired droplet spacing can be determined. There are several reasons for this improvement, but the basic one is that obtaining the image allows droplet shape to be taken into account in locating the center of gravity. Prior art systems based on gross occlusion do not take droplet shape into account. Even with good edge detection along the droplet trajectory, non-imaging systems cannot match the invention's precision.

Because the present invention provides for more precise control of droplet spacing and flow velocity, cell transit time between detection and breakoff is known with greater certainty. The length of stream segments that must be diverted to ensure proper cell sorting can be reduced. This means that more cells can be introduced per unit stream length for a given tolerance of coincidence. More cells can be sorted per unit time so that sorting throughput is increased. In addition, at least some existing droplet-deflection flow sorters already incorporate the required video hardware for the purpose of establishing the desired breakoff point. For such systems, the cost of implementing the present invention is merely marginal.

The control of droplet spacing can run without operator intervention. Furthermore, the video data used to regulate droplet spacing can be used, with little additional processing overhead, to determine the position of a first droplet and the gap between it and the jet. The deviations of these values from target values can be fed back to control the phase and amplitude of the droplet-generator drive signal. This, in turn, permits automated regulation of droplet breakoff point.

These and other features and advantages of the present invention are apparent from the description below with reference to the following drawings.

DESCRIPTION OF THE PREFERRED EMBODIMENTS

Figure 1:
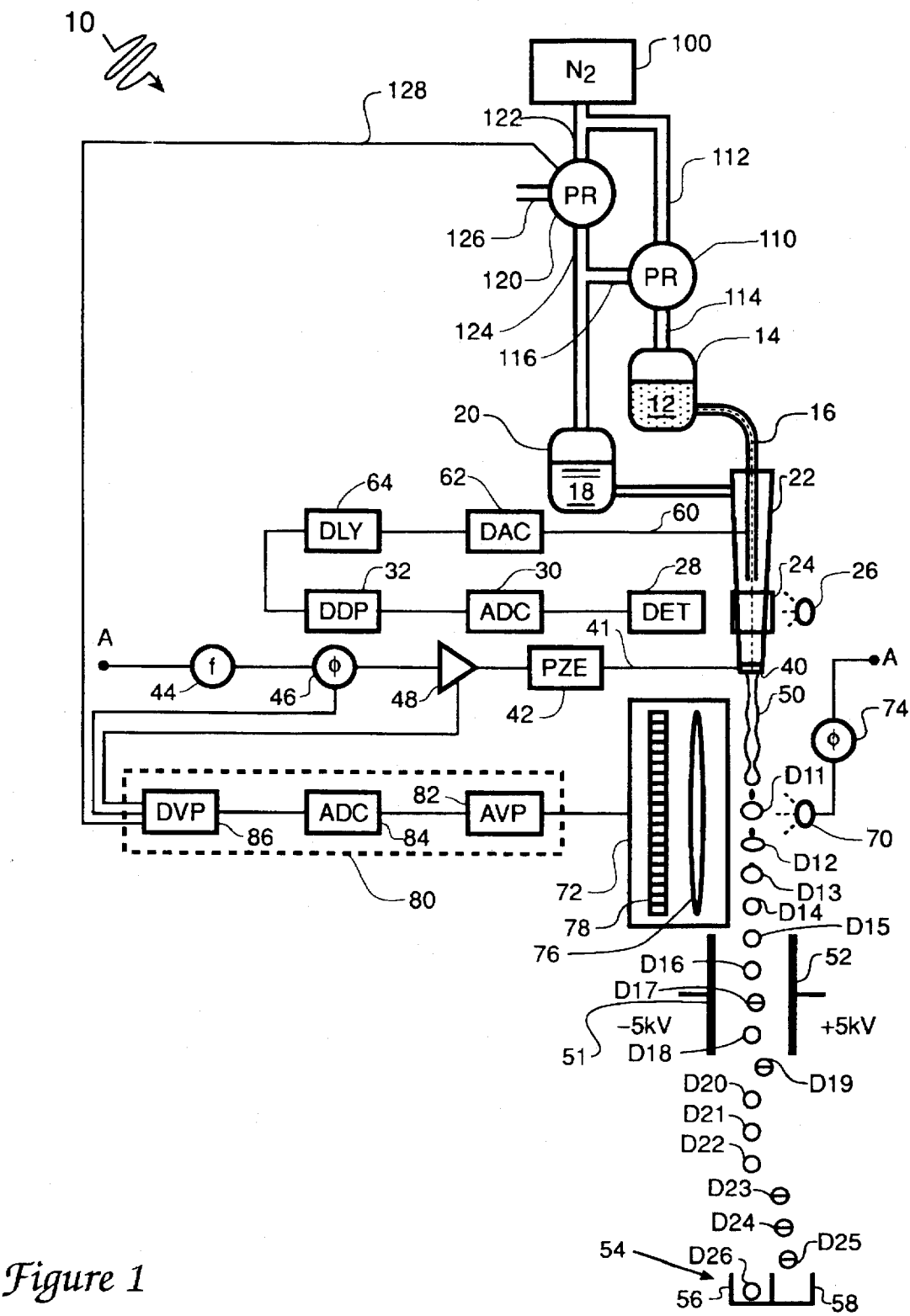
FIG. 1 is a schematic view of a cell sorting system in accordance with the present invention.

In accordance with the present invention, a cell sorter 10 provides for sorting of cells in a suspension 12 contained in a sample reservoir 14. Suspension 12 is forced by gas pressure into a narrow conduit 16 so that the cells are serialized in the resulting stream. As suspension 12 exits conduit 16, it encounters sheathing fluid 18 from a sheathing fluid reservoir 20. Sheathing fluid 18 radially confines suspension 12 as it traverses nozzle 22.

Incorporated along nozzle 22 is a cuvette 24 that serves as a window on the fluid flow through nozzle 22. Passing fluid is illuminated by a light source 26. Variations in scatter and/or fluorescence due to passing cells are detected by a detector 28. While only one light source and detector are shown used for cell characterization, it is understood that multiple sources and detectors can be used for more complex characterizations. The detector outputs are digitized by an analog-to-digital converter (ADC) 30. The digital data is then analyzed by digital data processor (DDP) 32 to determine whether a cell is present and, if so, if it is of interest.

A droplet generator 40 perturbs the stream just before it forms into a jet. Droplet generator 40 includes a piston that is coupled to nozzle 22 by an O-ring. The volume interior to the O-ring and between nozzle 22 and the piston is alternatively expanded and compressed to implement the stream perturbation. This action is effected by a mechanical linkage 41, which includes a lever, driven by a piezo-electric element 42. The frequency of perturbation is set at about 40 kilohertz (kHz) by a frequency generator 44. The drive phase is set by phase shifter 46, while the drive amplitude is set by an amplifier 48.

A jewel defining a jet orifice is disposed within the piston. Jet 50 forms as the stream is forced through the jet orifice. Jet 50 breaks up into droplets D11–D26 from jet 50 at the droplet generator drive frequency.

The droplets so formed follow a common initial trajectory through a pair of deflection plates 51 and 52. Plate 51 has a −5 kilovolt (kV) voltage applied to it, while plate 52 has a +5 kV voltage applied to it; this establishes a 10 kV potential difference between plates 51 and 52, which are spaced 1 centimeter (cm) apart to achieve an electric field of 10 kV/cm. A collector 54 contains two compartments 56 and 58. Compartment 56 is arranged to receive undeflected droplets, while compartment 58 is arranged to receive deflected droplets.

The intent is for compartment 58 to collect cells of interest to the exclusion of other cells and most of the suspension fluid. To this end, only droplets containing cells of interest should be charged, while other droplets are not. Furthermore, all charged cells (indicated in FIG. 1 by having a bar through the middle) should have the same charge so that they undergo the same deflection.

The charge (or lack of charge) on a droplet is determined by an electric field applied to the stream at the time the droplet breaks off from the stream. This electric field is established by a voltage supplied via a line 60 (relative to a grounded nozzle). The voltage is determined by a digital-to-analog converter (DAC) 62, which converts a digital output of digital data processor 32 to a voltage. The challenge is to apply the voltage at the appropriate time after a cell of interest is identified to take into account the transit time between detection and drop breakoff. Any portion of the transit time not consumed by detector 28, ADC 30, DDP 32, and DAC 62, is consumed by a digital delay (DLY) 64 interposed between DDP 32 and DAC 62. (Of course, the delay can be implemented elsewhere in the detection-to-voltage train.) This synchronizes the charging with the breakoff of the droplet bearing the cell of interest.

Jet 50 and droplets in the positions of droplets D11–D14 in FIG. 1 are imaged by a video system including a strobed light source 70 and a video camera 72. Strobed light source 70 is driven by frequency generator 44 so that acquired images are synchronized with droplet generation. The phase of strobe source 70 can be set by adjusting a phase shifter 74. Video camera 72 includes an objective lens assembly 76 and a charge-coupled device (CCD) 78. The output of video camera 72 is analyzed by video processor 80, including an analog video processor (AVP) 82, an analog-to-digital converter (ADC) 84, and a digital video processor (DVP) 86.

The outputs of video processor 80 represent deviations from target values for center-to-center droplet spacing, deviation of a first droplet from a reference position, and deviation of the spacing of the first droplet from jet 50 from a target value. The deviation in droplet spacing is fed back to a pressure regulator 120 and used to adjust the flow velocity of the fluid stream, which in turn is reflected in subsequently determined droplet spacings.

The pressure used to force suspension 12 and sheath fluid 18 from their respective reservoirs 14 and 20 is provided by a nitrogen pressure source 100. The precise pressure applied to suspension 12 is determined by a pressure regulator 110, while the precise pressure applied to sheath liquid 18 is determined by pressure regulator 120.

Pressure regulator 120 has a gas input 122, a gas output 124, a reference pressure input 126, and a control input 128. Gas input 122 is coupled to pressure source 100. Output 124 provides a constant pressure to sheath-fluid reservoir 20. This constant pressure is set by the signal at control input 128 relative to the ambient pressure presented at reference pressure input 126.

Pressure regulator 110 is similar in that its fluid input 112 is coupled to pressure source 100 and its fluid output 114 is coupled to the respective (suspension) reservoir 14. However, pressure regulator 110 is arranged so that its reference input 116 is coupled to fluid output 124 of pressure regulator 120. The control input of pressure regulator 110 is not shown, but it is set so that the pressure applied to suspension 12 is slightly positive to its reference, that is, the pressure applied to sheath fluid 18. Thus, when the output of video processor 80 changes the sheath fluid pressure output by regulator 120, the suspension fluid pressure output by regulator 110 is changed by a like amount.

The droplet breakoff point is not determined directly. Deviations of the first droplet from a reference position are fed back to phase shifter 46 so that the center-of-gravity of the first droplet in each video frame appears at the reference position. This phase adjustment has no important physical effect on droplet formation, but it allows the break-off point to be represented by the spacing of the first droplet from the jet.

Once the droplet is in the desired reference position, its spacing from the jet is determined. For example, the number of blank lines between the jet and the first droplet can be determined. The magnitude of the jet-droplet gap when the droplet is in the reference position corresponds to the position of the droplet break-off point. If the droplet at the reference position is not separated from the jet, the minimum thickness of the jet is measured and treated as a negative separation. The deviation of actual droplet separation is fed back to drive amplifier 48. If the droplet spacing is too large, drive amplitude is decreased; if the droplet spacing is too small or negative, drive amplitude is decreased.

For conceptual purposes, video processor 80 is presented with determining deviations in center-to-center spacings to adjust flow velocity, then determining deviations in first droplet position to adjust droplet phase, and then determining the gap between the jet and the first droplet to adjust droplet amplitude. In practice, these three loops can be run concurrently.

Figure 2:
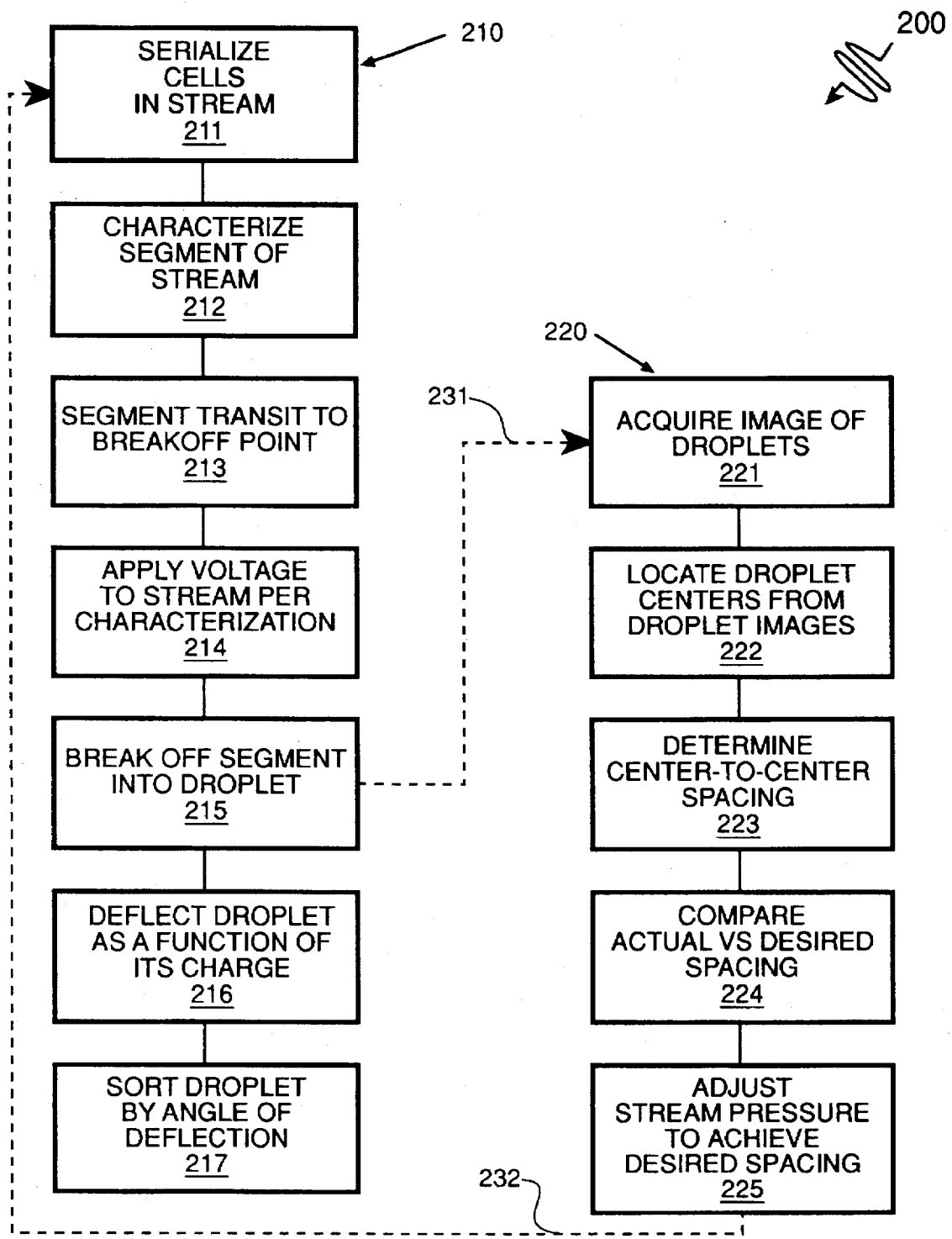
FIG. 2 is a flow chart of a method in accordance with the present invention used with the system of FIG. 1.

In accordance with the present invention, sorter 10 provides for implementation of a method 200 flow charted in FIG. 2. Method 200 includes two concurrently run tracks 210 and 220. Track 210 is basically method 200 from the perspective of the cells and droplets. Track 220 is the flow velocity control track using video imaging.

Droplet track 210 begins with serializing cells in a stream at step 211. This involves application of pressure to suspension reservoir 14 so that the suspension is forced into conduit 16. This step also involves the concurrent application of pressure to sheath-fluid reservoir 20 so that sheath fluid 18 and suspension 12 converge in nozzle 22.

Stream segments are characterized at step 212. This occurs at cuvette 24, as detector 28 responds to the contents of the passing stream. The characterization is completed by digital data processor 32. The characterized stream segment then is conveyed to a droplet breakoff point at step 213. However, delay 64 synchronizes stream charging with this transit.

A voltage is applied to the stream at step 214 as a function of the characterization at step 212. The purpose of this step is to set the charge of the next droplet to form. Where the next droplet is expected to contain no cell of interest, the voltage (with respect to ground, at which potential nozzle 22 is held) is selected so that no net charge is left on the droplet. If the droplet is expected to contain a cell of interest, the voltage is selected so that a predetermined negative charge is left on the droplet. The voltage required to establish the desired droplet charge depends, in part, upon the recent history of voltages applied to the stream. Accordingly, both the recent voltage history and the desired droplet charge are taken into account in setting the stream voltage.

The stream segment is formed into a droplet at step 215. Droplet formation is governed by the stream perturbations imposed by droplet generator 40 so that drops are of uniform size and spacing. The initial droplet trajectory extends between electrode plates 51 and 52. The field between plates 51 and 52 deflects droplets in proportion to their charge, at step 216. Uncharged droplets are not deflected, whereas charged droplets are deflected along a common post-deflection trajectory. The deflected droplets are collected in bin 58 of collector 54 at step 217. The undeflected droplets can be collected at bin 56.

Figure 3:
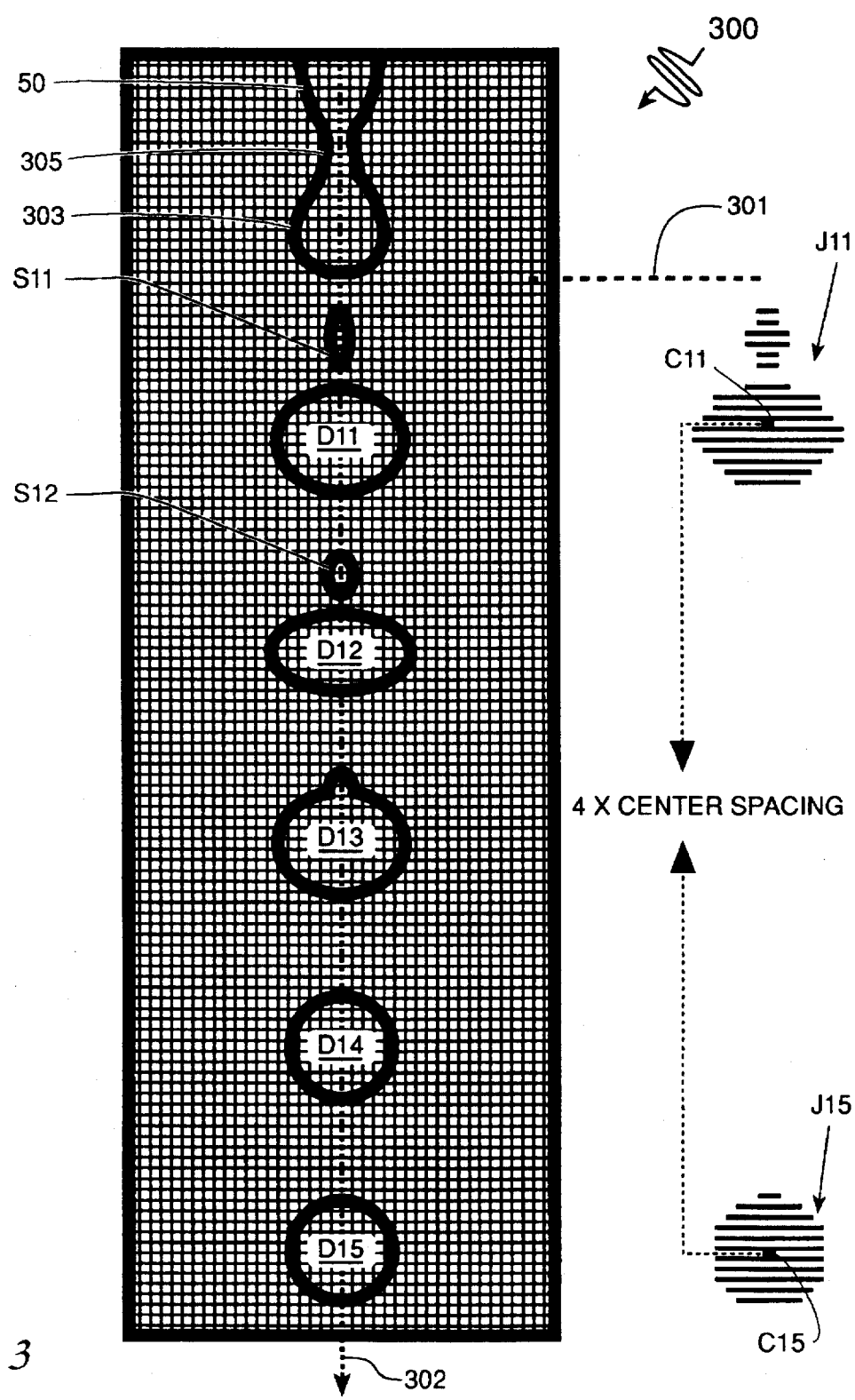
FIG. 3 is a schematic representation of an image and its analysis in accordance with the method of FIG. 2.

Track 220 begins with the acquisition of an image including at least two droplet subimages at step 221. Such an image is shown in FIG. 3 in the form of droplet profiles superimposed on a pixel grid corresponding to CCD 78. Since step 221 involves imaging droplets, it is related to track 210, step 215, as indicated by arrow 231.

The image is then processed to determine droplet spacing. In method 200, this objective is achieved in two steps. Droplet centers are located in step 222, then an "actual" droplet spacing is determined in step 223. These steps are considered in greater detail below.

The actual droplet spacing is compared with a desired droplet spacing at step 224. This step is performed by digital video processor 86. The output of digital video processor 86 is used to adjust stream velocity at step 225, completing one iteration of track 220. Accordingly, when the actual spacing is too low, digital video processor 86 sends a high error signal to pressure regulator 120, so that pressure, flow velocity, and droplet spacing increase. When the actual spacing is too high, digital video processor 86 sends a negative error signal to pressure regulator 120, lowering pressure, flow velocity and droplet spacing.

Steps 211–217 of track 210 operate concurrently in that at any given time, while some droplets are being collected, others are just being serialized, etc. Steps 211–217 are sequential as described from the perspective of the cells, stream segments, and droplets. From the operator's view, track 210 is a highly "pipelined" iterated process.

Track 220 is not pipelined in this fashion. To avoid oscillations, the effects of an adjustment in flow velocity should be stabilized by the time a succeeding determination of droplet spacing is made. A broken arrow 232 is used to indicate that the affects of adjustment step 225 need pass from reservoir to imaging field before the next image is acquired.

While track 210 is iterated at a much faster rate than track 220, they are run synchronously. As indicated in FIG. 1, video strobe 70 and droplet generator 40 are driven by the same frequency generator 44. Thus, droplet phase remains constant from image to image. This simplifies image processing.

Image processing proceeds as follows. The output of CCD 78 is a series of analog voltage values, each of which corresponds to a light intensity received by a respective pixel of CCD 78. Analog video processor 82 modifies these voltage values to correct for certain image artifacts. For example, droplets are distinguished from the background because they reflect and refract illumination away from CCD 78. However, light passing through a droplet diameter on axis with CCD 78 suffers minimal reflection and refraction. Accordingly, the center of a droplet image can have an intensity closer to that of the background than to that of the rest of the droplet. Thus, as seen by CCD 78, droplets are dark objects with light centers. Analog video processor 82 recognizes the light centers, since they are bracketed by dark regions. Analog video processor 82 converts the light centers to dark regions (by sampling and holding dark region voltages while light center regions are gated). The analog video processor includes an integrator, the output of which is a series of voltages pulses, each voltage corresponding to the width of a respective image line segment. Analog-to-digital converter 84 converts the series of voltages into a series of numbers that are received by digital video processor 86.

The input to digital video processor 86 is a series of numbers representing line widths. Thus, for example, to digital video processor 86, drop D15 looks like subimage J15 in FIG. 3.

The center of gravity for a droplet can be located as follows. Each droplet image contains a series of line segments. For example, droplet image J15 of droplet D15 contains 11 line segments. Each of these line segments represents a volumetric slice of the droplet. In the absence of asymmetrical forces operating orthogonal to trajectory 302, it can be assumed that the droplets have cylindrical symmetry about trajectory 302. Accordingly, the slices are circular disks one pixel deep and having diameters equal to the length of the corresponding line segment. The relative volumes of the slices are proportional to the squares of the diameters.

Assuming uniform droplet density, the center of gravity is located at the collective center of these volumetric slices. The distance D of the center of gravity for a droplet from reference line 301 is given by:

$$D = \frac{\sum_i d_i (l_i)^2}{\sum_i (l_i)^2}$$

where $d_i$ is the distance of a volumetric slice from reference line 301 and $l_i$ is its diameter (the length of the corresponding segment in the image).

For droplet D15, in image J15, the top line is 86 pixels from reference line 301 and is two pixels long. The next line is 87 pixels from reference line 301 and is 6 pixels long. The values for the other nine segments are 88,8; 89,10; 90,10; 91,10; 92,10; 93,10; 94,10; 95,8; 96,6. Inserting these values into the above equation yields a center of gravity approximately 91.47 pixels from reference line 301. The center of gravity is marked as C15 in droplet image J15.

Note that this is different from the midpoint between the top line and bottom line, which midpoint is 91 pixels from reference line 301. This demonstrates that the present invention provides for considerably more precision in the location of droplet centers than nonimaging methods that at best rely on edge detection. This advantage in precision is due primarily to the information as to drop shape obtained in the dimension orthogonal to the droplet trajectory. This advantage is attained even where, as is the case with droplet D15, the droplet is spherical. The advantages of the present invention are even more pronounced for nonspherical droplets.

While surface tension causes the droplets to eventually assume spherical form, they leave the jet deformed along the trajectory. Thus, at least the first few droplets represented in image 300 are nonspherical. This aspherical character is pronounced in droplet D13. Droplets D11 and D12 are even more anomalous in that they have respective satellites S11 and S12. Since these satellites eventually merge with their respective droplets, their volumes should be considered in determining droplet centers of gravity.

The present invention has little difficulty handling nonspherical droplets and satellites. For example, droplet D11 and its satellite S11 are represented by droplet image J11. From top to bottom, the lines of image J11 are 3,2; 4,2; 5,4; 6,4; 7,2; 8,2; 9,0; 10,4; 11,10; 12,10; 13,12; 14,14; 15,14; 16,12; 17,10; 18,8; and 19,6. Plugging these values into the center of gravity equation yields D=14.09 pixels from reference line 301. This point is marked as C11 in image J11. Note that the gap between satellite S11 and the main body of droplet D11 poses no special problem to the center of gravity calculation.

The difference in the center of gravity locations for D15 and D11 is 91.47−14.09=77.38. Since D15 and D11 are four periods apart, the average center of gravity spacing for the droplets is 77.38/4=19.35. Where the desired spacing is 19.60 pixels, for example, the digital video processor would have a positive output, increasing the pressure at both reservoirs, increasing flow velocity, and increasing droplet spacing.

Prior art methods of determining droplet spacing do not deal effectively with aspherical droplets and satellites. This limitation can be avoided by selected droplets far from the breakoff point. For example, one could determine droplet spacing from the spacing of droplets D14 and D15. However, it is preferable to choose droplets that are far apart because errors in center of gravity locations are divided by one plus the number of intervening droplets. Requiring the droplets to be spherical limits the range from which droplets are selected and thus the precision of the final spacing determination. This problem compounds the limitation that the prior art has in determining the center of gravity of a droplet even when it is spherical.

Once center of gravity C11 is located for droplet image J15, its position can be compared with a target position. The target can be given relative to reference line 301. If center of gravity C11 is not at the target position, the deviation is fed back to phase shifter 46 until subsequent first droplets in video images are properly located. Once a properly located droplet is established, the gap between it and the jet is determined and compared with a target gap value. In the present case, the gap is the number of lines between the image of droplet D11 and of jet 50. The nearby satellite can be ignored in measuring this gap.

In some cases, the droplet at the target position will not have completed its separation from jet 50. For example, the droplet at the target position might have the form of jet feature 303. In that case, there will be a last "waist" 305 of jet 50. The length of this waist is a negative measure of the first droplet gap. The resulting positive or negative deviation from the target gap is fed back to amplifier 48 to control drive amplitude, thus regulating the gap size.

It is noted that in FIG. 3, the image is about 40×120 pixels, while four times this resolution is commonly available for video imagers. This extra resolution can be used either to increase the precision with which drops are represented in the image or to increase the number of droplets in the image. In either case, further gains in the precision of droplet spacings are available. Furthermore, the video images can readily be acquired at a rate of 30 frames per second. Processing can be limited to droplets of interest, for example the first and last droplets in the field of view. Restricting the image data in this way keeps burdens on the video processing circuits at very modest levels.

Accordingly, the present invention provides an increase of at least an order of magnitude in the determination of droplet spacing. This yields a comparable increase in the precision with which flow velocity is controlled. This in turn means that transit time between detection and breakoff is known to greater certainty. This allows cells to be spaced more closely together in the stream, yielding a system with greater throughput.

While the foregoing embodiment addresses biological cell sorting, the present invention provides for sorting of a range of particle types in suspension. Furthermore, more complex sorting is provided for by using different charge magnitudes and polarities for the droplets. Obviously, a wide range of detection schemes for characterizing particles can be employed. While particular algorithms for locating centers of gravity are described, there are a range of alternative algorithms that can be employed to take advantage of the shape information available in an image. In fact, the method need not determine center of gravity locations specifically. Instead, spacing can be determined directly. These and other modifications to and variations upon the preferred embodiments are provided for by the present invention, the scope of which is limited only by the following claims.

What is claimed is:

1. A system for sorting particles in a suspension comprising:

flow means for serializing said particles in a stream having a flow velocity;

a droplet generator for generating droplets from said stream, said droplets having a common initial trajectory, each of said droplets being formed from a corresponding stream segment;

detection means for providing a characterization of the contents of each of said stream segments;

charging means for applying a time-varying electric field to said stream so that said droplets are charged as a function of characterization of the contents of the corresponding stream segments;

deflection means for deflecting said droplets so that their post-deflection trajectories are a function of their respective charges;

collection means for collecting said droplets in groups having common post-deflection trajectories;

imaging means for obtaining images, each of said images including subimages of at least two droplets;

image processing means for determining the deviation in the actual spacing of the centers of gravity for the droplets represented in each of said images from a target spacing between droplet centers of gravity; and flow velocity means for adjusting the flow velocity of said stream as a function said deviation so as to minimize said deviation.

2. A system as recited in claim 1 wherein said image processing means locates the center of gravity for a droplet by equating it with the point in the respective droplet subimage which would be the center of gravity assuming that the respective droplet has cylindrical symmetry about an axis along said common initial trajectory.

3. A method of sorting particles in a suspension comprising the steps of:

serializing said particles in a stream including said suspension, said stream having a flow velocity;

characterizing segments of the stream according to their particle contents so as to provide a characterization of each of said segments;

transporting each segment to a breakoff point;

applying a time-varying electric field to said stream so that the voltage applied is at least in part a function of said characterization of the segment at the breakoff point;

breaking off the segment at the breakoff point so that it forms a droplet having a charge that is a function of the characterization of the respective segment, said droplet having a trajectory;

deflecting the droplets by an angle that is a function of their respective charges;

collecting the droplets so that they are grouped as a function of their deflections;

acquiring an image of a subseries of said droplets after breakoff but before collection;

determining the deviation of the spacing of the centers of gravity of droplets in said image from a target droplet spacing; and adjusting flow velocity of said stream to reduce any discrepancy between said target spacing of the centers of gravity of droplets and subsequently determined actual spacings of the centers of gravity of droplets.

4. A method as recited in claim 3 wherein said determining step involves locating the center of gravity of a droplet by equating it with the image point that would be the center of gravity of the droplet assuming cylindrical symmetry about its trajectory.

* * * * *